US005414775A

United States Patent [19]

Scribner et al.

[11] Patent Number: 5,414,775

[45] Date of Patent: May 9, 1995

[54] NOISE ATTENUATION SYSTEM FOR VIBRATORY FEEDER BOWL

[75] Inventors: Kelvin Scribner, Linthicum; Doug Hodgson, Laurel, both of Md.

[73] Assignee: Noise Cancellation Technologies, Inc., Linthicum, Md.

[21] Appl. No.: 67,276

[22] Filed: May 26, 1993

[51] Int. Cl.[6] .................... A61F 11/06; H03B 29/00

[52] U.S. Cl. .................... 381/71; 181/206

[58] Field of Search .................... 181/206, 207, 208; 381/71, 94

[56] References Cited

U.S. PATENT DOCUMENTS

| | | | |
|---|---|---|---|
| 4,665,549 | 5/1987 | Eriksson et al. | 381/71 |
| 4,892,413 | 1/1990 | Vats | 188/200 |
| 5,091,953 | 2/1992 | Tretter . | |
| 5,146,505 | 9/1992 | Pfaff et al. | 381/86 |

FOREIGN PATENT DOCUMENTS

| | | | |
|---|---|---|---|
| 0076500 | 4/1991 | Japan | 381/71 |

OTHER PUBLICATIONS

Kinsler et al., "Fundamentals of Acoustics," John Wiley & Sons (1982) Contents, pp. ix–xvi.

*Primary Examiner*—Curtis Kuntz
*Assistant Examiner*—Ping W. Lee
*Attorney, Agent, or Firm*—James W. Hiney

[57] ABSTRACT

Active system for both attenuating mechanical vibration and the noise occasioned by the operation of vibratory feeder bowls in manufacturing having accelerometer (20) adjacent feeder bowl (21) and an inertial actuator (57) and a controller (59) to control both disturbances.

17 Claims, 4 Drawing Sheets

Fig.5
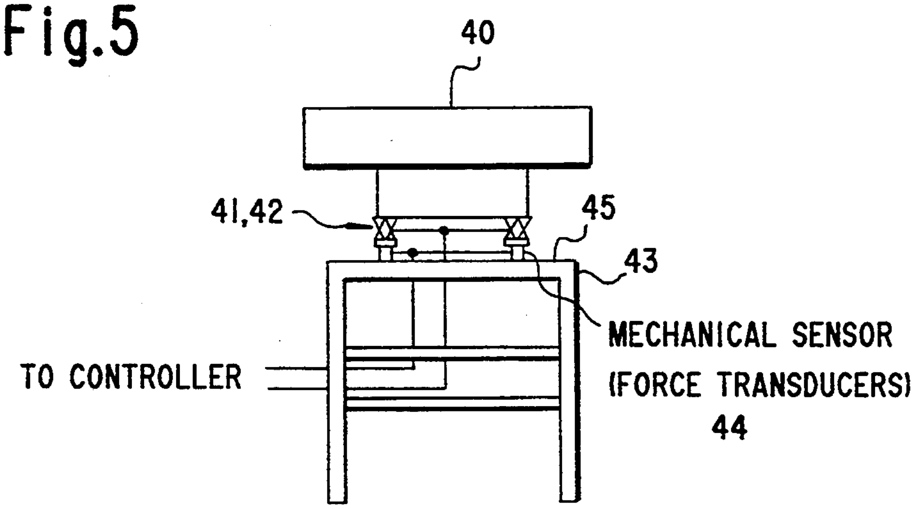
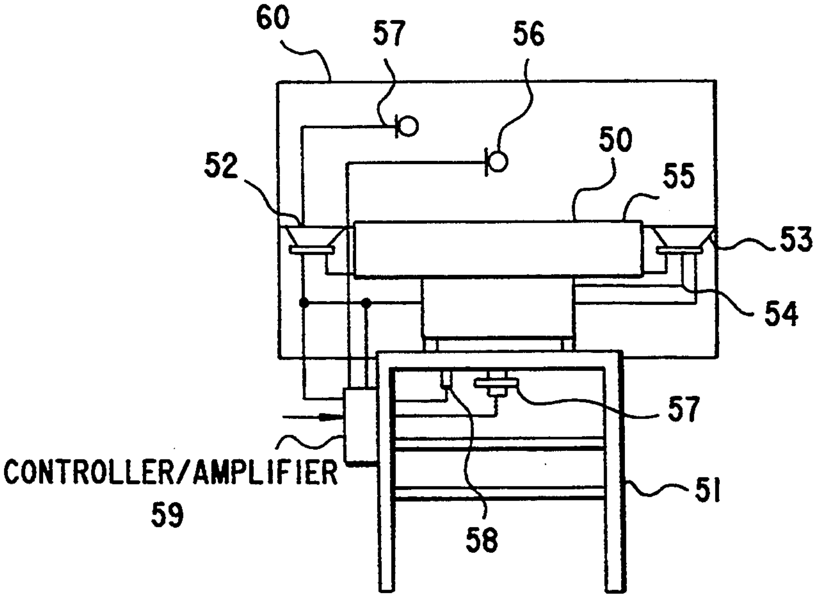
Fig.6

NOISE ATTENUATION SYSTEM FOR VIBRATORY FEEDER BOWL

BACKGROUND

Noise generated by a vibratory feeder bowl consists of two main components: noise generated by the parts being fed, and noise generated by the vibratory feeder bowl itself. Part noise is caused by part to part contact and pan: to bowl contact and usually manifests itself as a "rattle". Spectrally, this noise is broad band and usually above 300 Hz. Traditionally, this noise is treated passively by enclosing the vibratory feeder bowl. Such enclosures are frequently treated with sound absorbing foam as well as various damping treatments which are effective at higher frequencies, where part noise dominates.

The second component of vibratory feeder bowl noise is tonal noise caused by the motion of the vibratory feeder bowl. This noise is primarily periodic corresponding to the primarily sinusoidal excitation of the bowl. This periodic or tonal noise manifests itself as acoustic noise and mechanical vibration. Acoustic noise refers to the noise caused by the piston like motion of the vibratory feeder bowl. Acoustic noise is readily identifiable as a low tone or hum. This tone occurs at the primary operating frequency and its harmonics. Typical primary operating frequencies are 50, 60, 100, or 120 Hz. Vibratory feeder bowl users and manufacturers have attempted to attenuate this tonal noise by the use of enclosures. Although enclosures often redistribute the radiation pattern of the tonal noise, they typically do little to attenuate it.

Mechanical vibration is caused by the vibratory feeder bowl imparting vibration to the table on which it is mounted. Vibratory feeder bowls are usually mounted on soft elastomeric pads which reduce the forces transmitted to the mounting surface but do not eliminate them. The force transmitted through a passive mount is related to the ratio of the mass of the mounted device to the stiffness of the mount. Softer mounts allow less force to be transmitted to the mounting surface, thereby reducing the vibration caused by the vibratory feeder bowl. However, sorer mounts allow larger gross motions of the vibratory feeder bowl to occur when it is bumped or when parts are added. Such gross motions can cause the output track of the vibratory feeder bowl to exceed alignment tolerances causing parts jams and interrupting production. So in considering the stiffness of a mount, alignment tolerances are traded off against vibration transmitted by the mount.

Mechanical vibration can cause acoustic radiation. Because of the relatively large surface area of the table on which vibratory feeder bowls are usually mounted, small vibrations can cause effective acoustic radiation. Furthermore, vibration of the table induces vibration in the floor, which can also radiate acoustic energy. Table vibration often reduces the capability of the vibratory feeder equipment to feed parts. A reduction in vibration is desirable from a mechanical as well as acoustic standpoint.

SUMMARY OF THE INVENTION

The present invention reduces acoustic noise and mechanical vibration caused by vibratory feeder bowls or similar equipment. The device consists of an acoustic noise reduction system, a mechanical vibration reduction system, and a control system. The acoustic reduction system actively cancels noise generated by the piston like motion of the vibratory feeder bowl. The mechanical vibration reduction system actively cancels or prevents the transmission of forces from the vibratory feeder bowl which causes vibration in the table on which it is mounted. The control system monitors and adjusts the performance of the acoustic and mechanical vibration reduction systems.

Accordingly, it is an object of this invention to provide an active noise cancellation system for attenuating noise from a vibratory feeder bowl.

Another object of this invention is to provide an active noise cancellation system for canceling a dipole source of noise.

A still further object of this invention is to use inertial actuators in an active noise attenuation system to reduce vibration transmitted by vibratory feeder systems.

Yet another object is the use of piezoelectric devices to attenuate vibration transmitted by a vibratory feeder bowl.

These and other objects will become apparent when reference is made to the accompanying drawings in which

BRIEF DESCRIPTION OF THE DRAWING

FIG. 5 is a side view of a vibratory feeder bowl vibration attenuation system showing the use of isolation mounts and force transducers, FIG. 6 is a side/schematic view of a first embodiment of a vibratory feeder bowl noise reduction system.

ACOUSTIC NOISE REDUCTION SYSTEM

Because the pressure field resulting from the motion of a vibratory feeder bowl is similar to the field generated by a dipole source, the vibratory feeder bowl is well modeled as an oscillating source. One technique of spatially matching a dipole source is to place one or more additional dipole sources near the original source. Placed in the same orientation, and close to the original source, the pressure field generated by these additional sources will be spatially similar to the original source and can be used to effectively cancel the field generated by the original source.

Displacement of an acoustic actuator is measured in units of volume. The volume displacement of a given acoustic actuator may be visualized as the volume swept out by a surface of given area vibrating at a given amplitude. The acoustic actuator must produce at least the same volume displacement as the vibratory feeder bowl at the controlled frequencies. For example, if the acoustic actuator is a vibrating plane, and the effective area of the acoustic actuator is one tenth the area of the vibratory feeder bowl, the acoustic actuator must be capable of generating at least ten times the displacement of the vibratory feeder bowl.

The acoustic noise reduction system is intended to reduce the acoustic noise created by the piston like motion of the vibratory feeder bowl. The acoustic noise reduction system consists of an acoustic actuator and acoustic sensor.

ACOUSTIC ACTUATOR

The acoustic actuator must be spatially similar to, and be capable of producing the same volume displacement as the offending source. The piston like motion of the vibratory feeder bowl is best modeled as an acoustic dipole source. The acoustic actuator should also be well modeled as a dipole source. The acoustic portion of this invention is generalized to the use of oscillating sources to cancel noise from the offending dipole source.

Figure 1A:
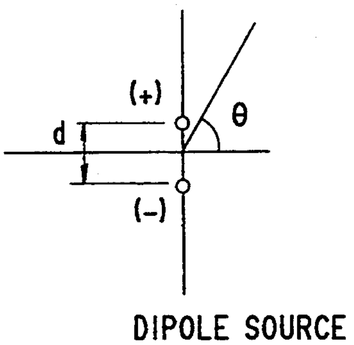
Fig.1(A) PRIOR ART
FIG. 1(A) illustrates an ideal representation of a dipole source consisting of two monopole sources separated by a distance, d, which is small compared to the wavelength.
Figure 1B:
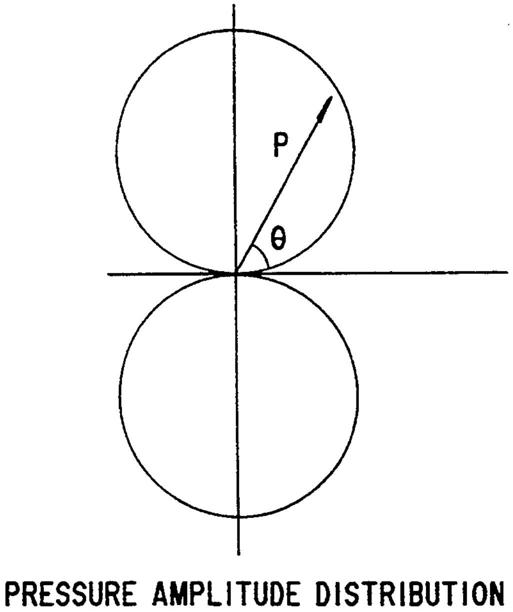
Fig.1(B) PRIOR ART
FIG. 1(B) illustrates the far field pressure amplitude distribution approximation resulting from the dipole source of FIG.1(A), where pressure amplitude is measured at a radii which is large compared to the separation distance, d of FIG.1(A), as a function of azimuth.

A dipole source is academically defined as two monopole sources oscillating 180 degrees out of phase at a given frequency, and separated by a given distance, which is small compared to the wavelength of sound at the excitation frequency. Such a source is illustrated in FIG. 1(A). At distances large compared to the source separation distances, the pressure field approximation exhibits a unique amplitude pattern. The pressure field is symmetric about the axis connecting the two sources, and anti symmetric about the plane which separates the two sources and is orthogonal to the axis connecting the sources. The pattern is illustrated by a pressure amplitude distribution diagram in FIG. 1B and in *Fundamentals of Acoustics,* Kinsler et al, 1982, John Wiley & Sons. The diagram depicts the variation of pressure amplitude as a function of azimuth from the source. The pressure field amplitude is zero in the plane separating the two sources and is at a maximum on the axis connecting the sources. The phase of the pressure field is anti symmetric about the plane separating the sources. All points in the pressure field on either side of this plane are in phase. Points on separate sides of this plane are 180 degrees out of phase.

One acoustic actuator which may be described as a oscillating source is an unenclosed loudspeaker. An unenclosed loudspeaker is well modeled as a oscillating source because the diaphragm or cone of the loudspeaker moves in a piston like fashion. A loudspeaker used to cancel acoustic noise from a vibratory feeder bowl differs in application from typical uses of loudspeakers. In most loudspeaker applications, it is desirable to prevent the pressure radiating from the back of the loudspeaker from destructively interfering with the pressure radiated from the front of the loudspeaker, thus increasing the radiative efficiency of the loudspeaker. This is accomplished by placing loudspeakers in cabinets, which vary in complexity, in order to increase the radiative efficiency over a frequency band of interest. However, the primary goal in using a loudspeaker to cancel noise from a dipole source is to ensure that the loudspeaker is spatially similar to the vibratory feeder bowl. Speaker cabinets could be used to increase the radiative efficiency of the loudspeaker in this application, provided the enclosed speaker retains the characteristics of a dipole.

ACOUSTIC SENSOR

The acoustic sensor must provide a signal to the controller which is indicative of the far field acoustic energy radiated. The degree to which the acoustic sensor is representative of the far field energy radiated is largely a function of how spatially similar the acoustic actuator is to those sources to which the acoustic sensor is sensitive. If the acoustic sensor is sensitive to sources which the acoustic actuators are not spatially similar to, the system may not attenuate overall acoustic radiation.

One example which causes far field performance deterioration is the effect of noise from adjacent, uncontrolled vibratory feeder bowls. In this example loudspeakers serve as the acoustic actuators and are placed around a controlled or primary vibratory feeder bowl. A microphone serves as the acoustic sensor and is placed above the primary vibratory feeder bowl. An uncontrolled or secondary vibratory feeder bowl, is close enough so that the microphone is sensitive to its noise. When the active acoustic reduction system is not operating, the noise measured by the microphone is partly due to the primary vibratory feeder bowl, and partly due to the secondary vibratory feeder bowl. However, the secondary vibratory feeder bowl is not sufficiently close to be considered spatially similar to the loudspeakers. When the acoustic reduction system operates, the loudspeakers are actuated so that the signal from the microphone is driven to zero. The acoustic result can be described as a summation of two signals: one which cancels the contribution of noise from the primary vibratory feeder bowl, and one which cancels the contribution of noise from the secondary vibratory feeder bowl. Because the loudspeakers are not spatially similar to the secondary vibratory feeder bowl, cancellation of its noise occurs locally, near the microphone only. At locations in the far field, the component of the loudspeaker signal which cancels noise from the secondary vibratory feeder bowl may interfere constructively with the noise from the secondary vibratory feeder bowl, increasing radiative efficiency. In general, the loudspeakers may be considered an additional source, which is roughly equal in strength to the secondary vibratory feeder bowl as measured at the location of the primary vibratory feeder bowl, with the control system not operating. So, noise from other sources which are measured by the acoustic sensor is in effect "echoed" by the acoustic reduction system and deteriorates far field performance.

The acoustic sensor can be designed to avoid far field performance deterioration due to additional sources which are spatially dissimilar to the acoustic actuator. The goal is to decrease sensitivity of the acoustic sensor to additional sources in comparison to the sensitivity of the sensor to the primary source. If the acoustic radiation resulting from the primary vibratory feeder bowl is considered "signal," and the acoustic radiation resulting from additional sources is considered "noise," then the goal can be restated as the desire to increase the signal-to-noise-ratio of the acoustic sensor.

Figure 2:
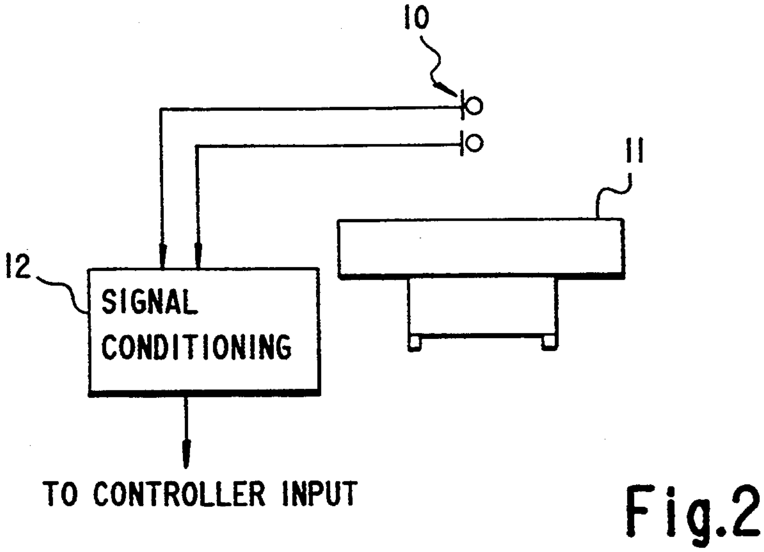
FIG. 2 is a schematic of a microphone array used to sense acoustic noise, where although not shown, the number of microphones in the array can be varied from one, in which case the array would be omni-directional, to many, in which case the array would be highly directional.

One design, as in FIG. 2, which increases the acoustic sensor signal-to-noise-ratio takes advantage of the known acoustic characteristics of a oscillating source. Signals from a plurality of microphones 10 placed in a physical array may be conditioned and combined 12 so that sensitivity is increased in the direction of the primary vibratory feeder bowl 11, but decreased in other directions, such as those of secondary sources. The array could be used to measure intensity and oriented such that the axis of sensitivity coincides with the axis of maximum intensity for a oscillating source parallel to the vibration of the vibratory feeding system "echoes" noise from secondary sources.

Figure 3:
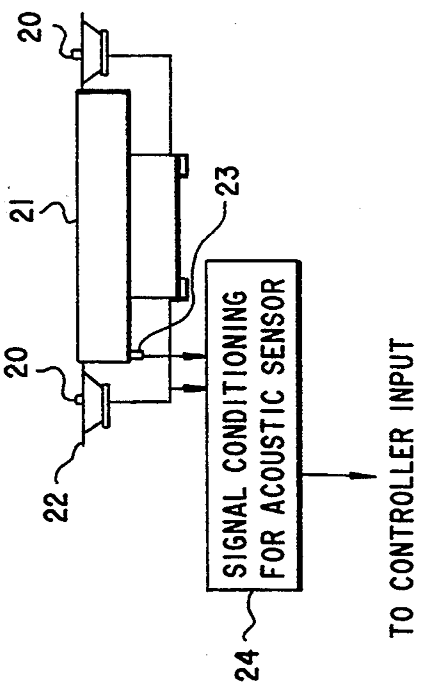
FIG. 3 is a schematic view of a vibratory feeder bowl acoustic noise attenuation system where accelerometers are used for acoustic reduction.

Another design which increases the acoustic sensor signal-to-noise-ratio is shown in FIG. 3, accelerometers are used to estimate acoustic radiation from the physical displacement of the surface of a given dipole source. Accelerometers 20, 23 are placed on the vibratory feeder bowl 21, and on cones or diaphragms of one or more loudspeakers 22. The signals from the loudspeaker accelerometers 20 and vibratory feeder bowl accelerometer 23 are weighed proportionally to the volume displacement of the device to which they are attached. The signals are then summed, conditioned as at 24 and used as the acoustic sensor. The resulting signal is proportional to the net volume displacement and therefore representative of the net acoustic energy radiated by the sum of the loudspeakers and vibratory feeder bowl. This signal is minimized by the controller via the acoustic actuators when the system is in operation.

Figure 4:
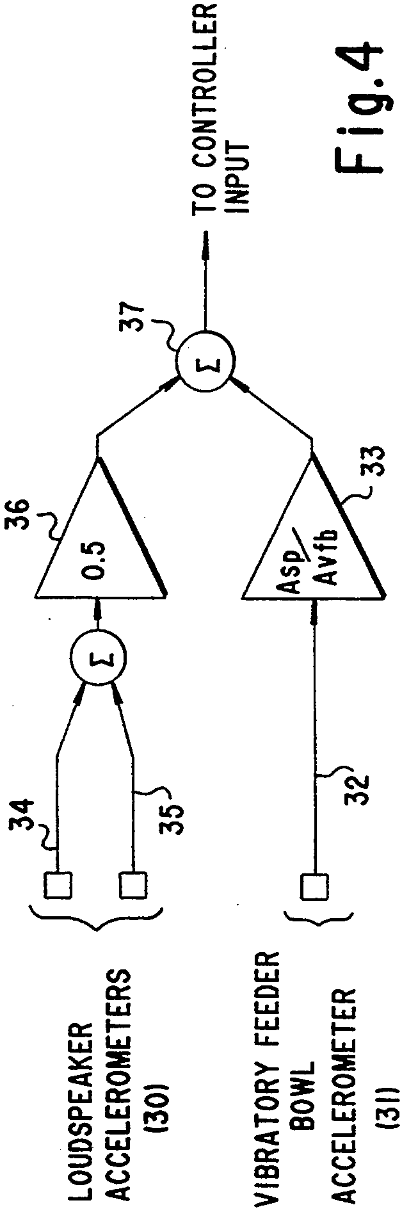
FIG. 4 is a schematic view of an accelerometer based acoustic sensor signal conditioning circuit.

FIG. 4 illustrates the signal conditioning portion of this process. Here, one accelerometer 30 is placed on each of two loudspeakers 22, and an accelerometer 31 is placed on the vibratory feeder bowl. Each accelerometer 30, 31 is assumed to have the same sensitivity. The signal 32 from the vibratory feeder bowl accelerometer 31 is conditioned at 33 by multiplication by a gain factor equal to the ratio of vibratory feeder bowl area (Avfb) to total speaker area (Asp). The signals 34, 35 from the loudspeaker accelerometers 34, 35 are averaged at 36 and summed at 37 with the conditioned vibratory feeder bowl accelerometer 31 signal. The result is representative of the volume displacement produced by the vibratory feeder bowl and loudspeakers.

The advantage of using accelerometers to estimate acoustic pressure or energy is that their sensitivity to secondary sources is negligible. The disadvantage of this technique is that gain errors in the signal conditioning result in an incorrect estimate of acoustic pressure or energy and deteriorate acoustic performance.

The speaker accelerometers 20 and vibratory feeder bowl accelerometers 21 of FIG. 3 may be replaced with microphones. Typically, these microphones would be placed within ten centimeters of the loudspeaker cones 22 and bowl portion of the vibratory feeder bowl 21 and would be used to estimate the position of the loudspeaker cone 22 and bowl portion of the vibratory feeder bowl 21, respectively. The signals from the microphones would be conditioned as in the discussion above, which refers to FIG. 4.

MECHANICAL VIBRATION REDUCTION SYSTEM

The mechanical vibration reduction system is intended to reduce the vibration induced in the support structure by the vibratory feeder bowl. The mechanical vibration reduction system consists of a mechanical actuator and mechanical sensor.

MECHANICAL ACTUATOR

The mechanical actuator may actuate to prevent vibration in the table on which the vibratory feeder bowl is mounted in two ways: force cancellation, and vibration isolation. Both techniques are well developed.

The force cancellation actuator must exert forces that are equal in magnitude and spatially similar to the forces caused by the vibratory feeder bowl. If the table is stiff at the controlled frequencies, spatial similarity may be achieved by placing the force actuator so that it exerts canceling forces at the center of action of the offending forces. If the axis of interest is vertical, the center of action may be near the centroid of the vibratory feeder bowl mounting points. In this case, a plurality of force actuators would be placed symmetrically about this centroid, or alternatively, a single force actuator would be placed at this centroid. If, however, the table is flexible at the controlled frequencies, one actuator should be placed beneath each mounting point to effectively cancel vertical forces. In such a case, it may be necessary to apply independent signals to each force actuator.

Vibration isolation, as in FIG. 5, is achieved by inserting active mounts 41, 42 between the vibratory feeder bowl 40 and the support frame 43. The active mounts are controlled to be extremely compliant at the bowl excitation frequencies. As a result, vibration is not transmitted to the table.

Vibratory feeder bowls induce table vibration in many axes. Because it impractical to cancel vibration in all axes, only the most offensive axes should be controlled. Vibration caused by vibratory feeder bowls tends to be primarily vertical. Also, vertical table motions radiate acoustic energy most effectively. So, if one must decide on a single axis to cancel vibration, the vertical axis is the natural choice.

MECHANICAL SENSOR

Placement of the mechanical sensor depends upon the type of sensor used, and the degree to which the mechanical actuators are spatially collocated with the offending source. If the mechanical actuators apply forces or compliance which spatially collocated with the offending forces or vibration, the mechanical sensor may be placed virtually anywhere uncontrolled motion can be measured in the axis of interest. However, if the forces are not spatially collocated with the offending sources, the sensor should be placed so as to be sensitive primarily to vibration in the axis of interest. The preferred location of the mechanical sensors is one that is sensitive to the vibration along the axis of interest.

An accelerometer is one example of a mechanical sensor. Used in the vertical axis, the accelerometer is mounted to the top or bottom surface of the table. Used in a horizontal axis, an accelerometer would be placed on the side of the frame corresponding to the direction of interest. Used in a rotational axis, two accelerometers are placed at locations off of the axis of rotation and the difference of the signals is used as the mechanical sensor signal.

If active isolation mounts are used as mechanical actuators, force transducers 44 may be used as mechanical sensors, as shown in FIG. 5. In this application the transducers are inserted between the isolation mounts 41, 42 and the support frame top 45. When force transducers are used as mechanical sensors, the isolation mounts actuate so that force is driven to zero at controlled frequencies. As a result a corresponding reduction in table vibration occurs.

CONTROL SYSTEM

The function of the control system is to provide signals to the mechanical and acoustic actuators so that the mechanical and acoustic sensor signals are driven to zero. The control system monitors signals from the sensors, and applies an output signal to the actuators which, after dynamically altered by the filters, amplifiers, actuators and the medium between the actuator and sensor, causes a reduction in the sensor signals. Often, sensors are sensitive to inputs to more than one actuator. If such is the case, the system is said to interact between channels. If, for example, the acoustic sensor is sensitive to signals sent to the mechanical actuator, the controller would need to account for this in driving the signal from the acoustic sensor toward zero. This process is described in detail in U.S. Pat. No. 5,091,953, entitled "Repetitive Phenomena Cancellation Arrangement with Multiple Sensors and Actuators" by Steven A. Tretter which is herein incorporated by reference in its entirety.

DETAILED DESCRIPTION OF THE PREFERRED EMBODIMENTS

Enclosed System

FIG. 6 depicts the first embodiment of the vibratory feeder bowl noise reduction system enclosed within a passive enclosure 60. Here a vibratory feeder bowl 50 is mounted to a table 51. Two loudspeakers 52,53 are mounted to the support structure 54 such that the cones or diaphragms of the loudspeakers are parallel to the plane of the base of the bowl portion of the vibratory feeder bowl 50. The loudspeakers 52, 53 are positioned vertically above the table 51 to be approximately the same height as the bowl portion 55 of the vibratory feeder bowl 50. The loudspeakers 52, 53 are sized so that the loudspeakers are capable of producing the same volume displacement as the vibratory feeder bowl at the frequency of vibratory feeder bowl oscillation (typically 50, 60, 100 or 120 Hz).

The acoustic sensor 56 is depicted as a microphone placed above the vibratory feeder system in FIG. 6. The microphone may be placed anywhere the pressure field of the feeder system is measurable. Ideally, the microphone 56 is placed above or below the vibratory feeder bowl 50 since the sound field of an oscillating source is largest along the central axis parallel to the oscillating motion.

The mechanical vibration reduction system is depicted as an inertial actuator 57 and an accelerometer 58 in FIG. 6. Actuator 57, which produces a periodic force on the magnet causing it to move periodically. This force is also exerted on the underside of the mounting surface 51 as a reaction force. The inertial actuator must be capable of exerting the same periodic force on the mounting surface 50 as the vibratory feeder bowl exerts on the mounting surface 51.

Placement of the actuator 57 depends on the stiffness of the table 51. If the table top 51 is stiff at the controlled frequencies, and bending of the table top 51 is negligible at this frequency, the inertial actuator 57 may be placed centrally beneath the vibratory feeder bowl 50, as shown in FIG. 6. However, if the table 51 is flexible at controlled frequencies, one inertial actuator 57 should be placed beneath each mounting point of the vibratory feeder bowl 50.

The mechanical vibration sensor is depicted in FIG. 6 as an accelerometer 58 mounted next to the inertial actuator 57. The stiffness of the table 51 at controlled frequencies must also be considered in placing the accelerometer 58. If the table 51 is stiff, and moves rigidly at controlled frequencies, the accelerometer 58 may be placed anywhere on the top or bottom surface of the table 51. If the table 51 is flexible at controlled frequencies, the accelerometer 58 should be placed close to the inertial actuators 57.

The control system is depicted as a box 59 containing electronics in FIG. 6. Here, the control system 59 receives signals from microphone 56 and accelerometer 58. It provides signals through an amplifier 59, to the loudspeakers 52,53 and inertial actuator 57 such that the signals from the sensors 56, 58 are driven to zero at the vibratory feeder bowl operating frequency and perhaps harmonics of the vibratory feeder bowl operating frequency. This is accomplished through what is known as destructive interference. In the case of the acoustic system, the control system 59 sends a periodic signal to the loudspeakers 52,53 such that they produce sound at the microphone 56 which is the opposite of the sound produced by the vibratory feeder bowl 50, the inertial reduction system, and other sources. The sound produced by the loudspeakers 52, 53 at the microphones is equal in amplitude and phase shifted by 180 degrees, as compared to the sound radiated by the vibratory feeder bowl 50, vibration reduction system, and other sources. As a result, the pressure or sound at the microphone 56 is driven to zero at those frequencies controlled. Also, because the loudspeakers 52, 53 exhibit the quality of being spatially similar to the vibratory feeder bowl 50, the energy radiated by the entire system is reduced. The control system used which accomplishes this is described in U.S. Pat. No. 5,091,953.

Care must be taken to ensure the contribution of sound from sources other than the controlled vibratory feeder bowl 50 is small compared to the sound produced by the bowl when the cancellation system is operating. If other sources are significant, a reduction of sound pressure at the microphones 56 may not correspond to a significant far field noise reduction.

Vibration of the mounting surface is reduced by the vibration reduction system using the same principle of destructive interference. In this case, the control system 59 sends a periodic signal to the inertial actuator 57 such that it produces a vibration at the accelerometer 58 which is the opposite of the vibration produced by the vibratory feeder bowl 50 and acoustic reduction system. The vibration produced by the inertial actuator 57 at the accelerometer 58 is equal in amplitude and phase shifted by 180 degrees, as compared to the vibration produced by the vibratory feeder bowl 50, acoustic control system, and other sources. As a result, vibration as measured by the accelerometer 58 is driven to zero at the controlled frequency. Also, because the inertial mounts 57 are spatially similar to the vibratory feeder bowl 50 from the standpoint of table 51 vibration, the overall vibration of the table is reduced. Physically, the inertial actuators 57 apply a periodic vertical force (at the controlled frequencies) to the table 51 which is equal and opposite the sum of the vertical component of forces (at the controlled frequencies) applied by the vibratory feeder bowl 50 and the floor. Because the table 51 vibration is virtually eliminated, it no longer acoustically radiates noise. In many cases, the mechanical vibration reduction system is necessary for acceptable acoustic reduction. Such is the case in applications where acoustic radiation due to vibration of the table 51 and floor is significant compared to acoustic radiation due to the piston like motion of the vibratory feeder bowl 50.

Additional axes of control may be applied when additional equipment is mounted to the table 51. The requirement for additional axes would stem from the severity of vibration in those axes. For example, if a linear pans track causes severe vibration in the vertical, rotational, and horizontal directions, additional channels of control could be added to cancel vertical force, horizontal force, and moments exerted by the parts track on the table. Although controlling force and vibration in additional axes significantly reduces mechanical vibration, additional acoustic reductions may not be as significant as those achieved by reducing vertical vibration. This is because table vibration in the horizontal and rotational directions does not radiate acoustic energy as efficiently as table vibration in the vertical direction.

Unenclosed System

Figure 7:
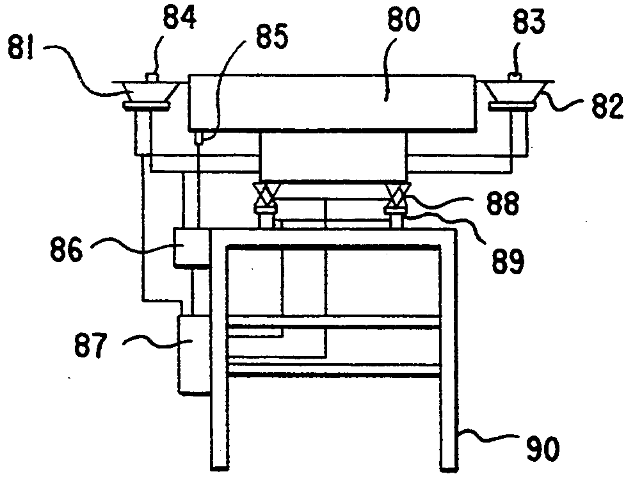
FIG. 7 is a side/schematic view of a second embodiment of a vibratory feeder bowl noise reduction system.

A second embodiment of the device is shown in FIG. 7. In this case, no enclosure has been placed around the vibratory feeder bowl 80. Once again, two loudspeakers 81,82 are mounted horizontally so that their cones or diaphragms are parallel to the plane of the bowl portion of the vibratory feeder bowl 80. They are vertically positioned to be at approximately the same level as the bowl portion of the vibratory feeder bowl 80.

The acoustic sensor in this embodiment takes the form of multiple accelerometers 83, 84, 85. One accelerometer 83, 84 is mounted to each loudspeaker 81, 82 cone, and to the bowl portion of the vibratory feeder bowl 85. The accelerometers 82, 83, 85 measure acceleration in the vertical direction. The signals from each loudspeaker 81, 82 accelerometer are averaged by the signal conditioning box 86, creating a resultant loudspeaker acceleration signal. The signal from the accelerometer 85 mounted on the vibratory feeder bowl 80 is multiplied by a weighting factor and summed with the averaged signal from the loudspeaker accelerometers 83, 84, as shown in FIG. 4. The weighting factor is nominally the ratio of the total cone or diaphragm area of the loudspeakers 81, 82 to the cross sectional area of the bowl portion of the vibratory feeder bowl 80. This weighted sum of the signals then input to the controller amplifier 87, taking the place of the microphone signal in the previous embodiment. The purpose of using a weighted summation of acceleration signals is to decrease the sensitivity of the system to additional acoustic sources, such as other vibratory feeder bowls, thereby enhancing far field performance.

A similar concept is employed in the mechanical vibration reduction system of this second embodiment. Active isolation mounts 88 are used as mechanical actuators and force transducers 89 are used as mechanical sensors. The mounts 88 and transducers 89 are inserted in series between the mounting points of the vibratory feeder bowl 80 and the table 90. In this case, the active isolation mounts 88 reduce the force between the vibratory feeder bowl 80 as measured by the force transducers 89. Although vibration due to the operation of the vibratory feeder bowl 80 is eliminated, vibration caused by other sources such as other equipment or vibration transmitted from the floor is not necessarily reduced. The floor induced table vibration is reduced.

The control system 87 operates in the same manner as in the first embodiment. It sends the necessary signal to each actuator 81, 82, 88 so that the signals from the acoustic and mechanical sensors 83, 84, 85, 89 are driven to zero at the controlled frequency.

Having described the invention and the preferred embodiments attention is directed to the claims.

We claim:

1. A system for attenuation of tonal noise in a vibratory feeder bowl mounted atop a support means, said system comprising a noise attenuation system means associated with said vibratory feeder bowl for canceling acoustic noise emanating from said bowl during operation, a vibration attenuation system means associated with said support means and for reducing vibration on said support means to attenuate tonal noise caused by mechanical vibration of said support means during bowl operation, and control means for sensing said acoustic noise and mechanical vibration and to provide signals to said noise attenuation and vibration attenuation means to effect operation thereof.

2. A system as in claim 1 wherein said noise attenuation system means is enclosed within a passive enclosure means.

3. A system as in claim 1 wherein said noise attenuation system includes at least one speaker means.

4. A system as in claim 3 wherein said speaker means is adapted to be mounted in the same plane as said vibratory feeder bowl.

5. A system as in claim 4 including means to measure the acoustic noise.

6. A system as in claim 5 wherein said speaker means has an accelerometer means associated therewith to provide a signal for said control means.

7. A system as in claim 5 wherein said speaker means has a microphone means associated therewith to provide a signal for said control means.

8. A system as in claim 5 including a vibratory feeder bowl accelerometer means to provide a signal for said control means.

9. A system as in claim 5 including a vibratory feeder bowl microphone means to provide a signal for said control means.

10. A system as in claim 1 wherein said noise attenuation system includes means for canceling a first dipole noise source by placing additional dipole source means around said first dipole noise source.

11. A system as in claim 1 wherein said vibration attenuation system means includes a vibration sensor means.

12. A system as in claim 11 wherein said vibration attenuation system includes inertial actuator means associated with said support means to produce a counter vibration to attenuate vibrations sensed by said vibration sensor means.

13. A system as in claim 12 wherein said support means comprises a table with a planar top, said sensor means and said inertial actuator means being attached to said planar top.

14. A system as in claim 11 wherein said vibration sensor means is an accelerometer.

15. A system as in claim 1 wherein said vibration attenuation means comprises active isolation mount means between said support means and said vibratory feeder bowl.

16. A system as in claim 15 including residual signal means to provide a residual signal to said control means which in turn, said residual signal to zero.

17. A system as in claim 1 and including a bowl accelerometer means and loudspeaker accelerometer means and a signal conditioning means to produce a weighted average of the signals from said loudspeaker accelerometer means and to produce a weighted sum of the result with the signal from said bowl accelerometer means to provide an output representative of the acoustic volume displacement produced by said bowl and loudspeaker means.

* * * * *